US006867602B2

(12) United States Patent
Davis et al.

(10) Patent No.: US 6,867,602 B2
(45) Date of Patent: Mar. 15, 2005

(54) METHODS AND SYSTEMS FOR CAPACITIVE BALANCING OF RELATIVE HUMIDITY SENSORS HAVING INTEGRATED SIGNAL CONDITIONING

(75) Inventors: Richard A. Davis, Plano, TX (US); Richard A. Kirkpatrick, II, Richardson, TX (US); Steve R. Foote, Arlington, TN (US); Ron Foster, Fayetteville, AR (US)

(73) Assignee: Honeywell International Inc., Morristown, NJ (US)

( * ) Notice: Subject to any disclaimer, the term of this patent is extended or adjusted under 35 U.S.C. 154(b) by 76 days.

(21) Appl. No.: 10/322,152

(22) Filed: Dec. 18, 2002

(65) Prior Publication Data

US 2004/0008041 A1 Jan. 15, 2004

Related U.S. Application Data (63) Continuation-in-part of application No. 10/192,451, filed on Jul. 9, 2002, now Pat. No. 6,724,612.

(51) Int. Cl.[7] .............................................. G01R 27/26
(52) U.S. Cl. ...................... 324/664; 324/658; 324/660; 324/663; 324/656; 324/686
(58) Field of Search .............................. 324/658, 660, 324/663, 664, 656, 686; 361/328, 330

(56) References Cited

U.S. PATENT DOCUMENTS

| | | | | |
|---|---|---|---|---|
| 3,665,570 A | * | 5/1972 | Brooks ....................... | 29/25.42 |
| 4,190,854 A | * | 2/1980 | Redfern ..................... | 257/532 |
| 4,470,096 A | | 9/1984 | Guertin ...................... | 361/277 |
| 4,564,882 A | | 1/1986 | Baxter et al. ................ | 361/286 |
| 4,831,325 A | | 5/1989 | Watson, Jr. .................. | 324/61 |
| 4,924,064 A | | 5/1990 | Stormbom et al. ..... | 219/121.69 |
| 5,296,819 A | | 3/1994 | Kuroiwa et al. ............ | 324/670 |
| 5,402,075 A | | 3/1995 | Lu et al. ..................... | 324/664 |
| 5,408,381 A | | 4/1995 | Thoma et al. .............. | 361/286 |
| 6,222,376 B1 | | 4/2001 | Tenney, III ................. | 324/664 |
| 2002/0078733 A1 | | 6/2002 | Seakins et al. ............. | 73/29.02 |
| 2002/0114125 A1 | | 8/2002 | Toyoda et al. .............. | 361/286 |
| 2002/0141136 A1 | | 10/2002 | Toyoda et al. .............. | 361/302 |
| 2004/0008471 A1 | | 1/2004 | Davis et al. ............. | 361/306.3 |

FOREIGN PATENT DOCUMENTS

| | | | |
|---|---|---|---|
| DE | 1938767 | 2/1971 | |
| FR | 2004008471 A1 | 1/2004 | ............ H01G/5/04 |

OTHER PUBLICATIONS

PCT Notification of Transmittal of the International Search Report or the Declaration Date of Mailing: Jun. 15, 2004, PCT/US 03/40742.

* cited by examiner

*Primary Examiner*—N. Le
*Assistant Examiner*—John Teresinski
(74) *Attorney, Agent, or Firm*—Kris T. Fredrick; Kermit D. Lopez; Luis M. Ortiz (57) ABSTRACT

Methods of and systems for balancing the capacitance of a common series capacitive circuit in a semiconductor-based sensor, such as a humidity sensor, are described. Relative humidity sensors can provide measurements via a series capacitive circuit including a humidity-sensitive dielectric separating a common top plate and first and second bottom plates associated with a first and second capacitor, Cx1 and Cx2. For proper operation, the common top plate should be in capacitive balance. Capacitive balance can be achieved by creating voids within and/or along the common top plate of the sensor. A system for creating voids can include a precision cutting instrument, a measuring device for enabling the measurement of capacitance of at least one of the common series capacitive circuit, Cx1 and Cx2, and power provided from a voltage source.

19 Claims, 9 Drawing Sheets

METHODS AND SYSTEMS FOR CAPACITIVE BALANCING OF RELATIVE HUMIDITY SENSORS HAVING INTEGRATED SIGNAL CONDITIONING

PRIORITY TO RELATED APPLICATION

This present invention is a continuation-in-part (CIP) of U.S. patent application Ser. No. 10/192,451, filed Jul. 9, 2002 now U.S. Pat. No. 6,724,612, entitled, "Relative Humidity Sensor With Integrated Signal conditioning."

TECHNICAL FIELD

This invention relates to semiconductor wafer-based devices. More particularly the present invention relates to semiconductor-based sensors. The present invention is also related to humidity sensors. More particularly, the present invention is related to methods and systems of balancing the capacitive values of a top plate associated with a semiconductor-based relative humidity sensor including integrated signal conditioning.

BACKGROUND OF THE INVENTION

Solid-state semiconductor devices are found in most electronic components today. Semiconductor-based sensors, for example, are fabricated using semiconductor processes. Humidity sensors are but one class of semiconductor-based sensors finding many industrial applications. Modern manufacturing processes, for example, generally require measurement of moisture contents corresponding to dew points between –40° C. and 180° C., or a relative humidity between 1% and 100%. There is also a need for a durable, compact, efficient moisture detector that can be used effectively in these processes to measure very small moisture content in gaseous atmospheres.

Humidity can be measured by a number of techniques. In a semiconductor-based system, humidity can be measured based upon the reversible water absorption characteristics of polymeric materials. The absorption of water into a sensor structure causes a number of physical changes in the active polymer. These physical changes can be transduced into electrical signals which are related to the water concentration in the polymer and which in turn are related to the relative humidity in the air surrounding the polymer. Two of the most common physical changes are the change in resistance and the change in dielectric constant, which can be respectively translated into a resistance change and a capacitance change. It has been found, however, that elements utilized as resistive components suffer from the disadvantage that there is an inherent dissipation effect caused by the dissipation of heat due to the current flow in the elements necessary to make a resistance measurement. The result is erroneous readings, among other problems.

Elements constructed to approximate a pure capacitance avoid the disadvantages of the resistive elements. It is important in the construction of capacitive elements, however, to avoid the problems that can arise with certain constructions for such elements. In addition, there can also be inaccuracy incurred at high relative humidity values where high water content causes problems due to excessive stress and the resulting mechanical shifts in the components of the element. By making the component parts of the element thin, it has been found that the above-mentioned problems can be avoided and the capacitance type element can provide a fast, precise measurement of the relative humidity content over an extreme range of humidity as well as over an extreme range of temperature and pressure and other environmental variables.

Humidity sensing elements of the capacitance sensing type usually include a moisture-insensitive, non-conducting structure with appropriate electrode elements mounted or deposited on the structure along with a layer or coating of dielectric, highly moisture-sensitive material overlaying the electrodes and positioned so as to be capable of absorbing water from the surrounding atmosphere and reaching equilibrium in a short period of time. Capacitive humidity sensors are typically made by depositing several layers of material on a substrate material.

Semiconductor-based humidity sensors are well known in the art. For example, U.S. Pat. No. 4,564,882, entitled "Humidity sensing element", issued Jan. 14, 1986, discloses a capacitance humidity sensing element. The sensing element structure includes a substrate and a set of interdigitated electrodes deposited on the substrate surface. A first water permeable polymer film is deposited over the electrodes and a conductive mesh is formed over the first polymer film. A second polymer film is deposited over the mesh, burying the mesh between the two polymer films. The spacing between openings of the mesh is less than the thickness of the second polymer film. The square of the sum of the two polymer film thicknesses is minimized so that the response time is minimized. The mesh conductivity is made greater than a minimum value so that the resistive component of the impedance is small compared with the capacitive impedance, and thus the device impedance is independent of any instabilities in the conductive mesh impedance.

U.S. Pat. No. 6,222,376 entitled "Capacitive moisture detector and method of making the same," issued Apr. 24, 2001, to Tenney, discloses a multi-layer polymer RH sensor. The Tenney patent describes an improved capacitive moisture detector that includes a ceramic substrate with a plurality of layers of interdigitated electrodes and a plurality of interleaved moisture sensitive dielectric layers. Alternate electrodes are electrically coupled to provide two electrical contacts and a circuit representing multiple capacitors connected in parallel. According to an exemplary embodiment, six layers are provided, resulting in a structure presenting five parallel connected capacitors, thereby providing a total capacitance of the detector which is ten times that of previous detectors having the same footprint. According to a preferred embodiment of the Tenney invention, each dielectric layer is made relatively thin to effectively decrease the distance between the plates of each of the five capacitors. Since capacitance is inversely proportional to the distance between the dielectric layers, the thinness of the electrodes in the present invention also serves to increase capacitance. According to another preferred embodiment of the Tenney patent, a floating porous conductive film is provided over the sixth electrode to contain the field of the top capacitor and render the detector immune from the effects of surface contaminants.

U.S. Pat. No. 4,831,325, entitled "Capacitance measuring circuit", issued May 16, 1989, to Watson, discloses yet another semiconductor-based sensor for measuring humidity. In the Watson patent, a variable capacitor, which may be a humidity-sensitive capacitor, and a fixed reference capacitor are connected at a node. The node is clamped at a reference potential during a first phase of a two-phase measuring cycle as the variable capacitor is charged to a fixed voltage and the fixed capacitor is charged to a feedback voltage. The node is unclamped during the second phase and the capacitors are connected in a series loop to allow a redistribution of the charge in the capacitors or force a reversal of that charge with a voltage source. The deviation of the node from its reference potential after charge redistribution occurs is used as input to a feedback circuit that integrates that deviation over a number of cycles until it provides a feedback voltage of magnitude sufficient to cause the node deviation to be reduced to zero. A second reference capacitor can be supplied to provide an offset. The capacitors are constructed by simultaneous deposition on a substrate of a first plate followed by a dielectric film and a second plate. The second plate of the variable capacitor is porous to admit water molecules and the second plate of the fixed capacitor is impervious to water. According to Watson, simultaneous deposition provides similar characteristics for the capacitors.

An electrical connection problem has been found to reside in some semiconductor humidity sensor designs as described in, but not limited to, the Watson patent. Failed electrical connection can result where a large step height exists between the conductive electrical plates and the electrical interconnects, particularly during thermal/humidity cycling due to the relatively high Temperature Coefficient of Expansion of the sensing medium (e.g., dielectric film, polyimide insulator) and the swelling and shrinking of the sensing medium. By this mechanism, changing humidity or temperature can disconnect the sensing capacitor system from the chip electronics, or at least change the capacitive value of the sensor arrangement.

The present inventors have found that there is a need for improved humidity sensor designs. In view of the above-identified shortcomings of previous devices, the present inventors have invented an improved relative humidity sensor. The present inventors have also invented method and systems for balancing capacitive values associated with sensors that utilize a top plate that is common to two series capacitors, such as the improved relative humidity sensor described herein. Accordingly, the present invention is described and presented as a means to address the shortcomings currently found in present humidity sensor devices.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

A sensor, such as an integrated relative humidity sensor (IRHS) including a planar humidity sensitive capacitor structure can include: a thin porous platinum top plate, a humidity sensitive polyamide dielectric, and a metal (e.g., titanium-tungsten) bottom plate. Two capacitors of the sensor can be effectively wired in series such that the metal bottom plates form the independent, electrically driven connections, and the thin top layer, which can be made of platinum, can be used to form a top plate of the sensor configuration and a common floating series interconnection for the two capacitors (e.g., $Cx1$ and $Cx2$). The floating series interconnection has been shown to eliminate problems associated with interconnection between the prior art thin platinum plate to thick aluminum or metal interconnections. But changes in humidity, such as would be common in a humidity sensor, can influence properties of the top plate. Moisture and humidity affecting the dielectric properties of a common top plate can thereby change the capacitive value of the series capacitive circuit enabled by the top plate, which is common to $Cx1$ and $Cx2$.

In accordance with a preferred embodiment of the present invention, a common top plate associated with providing capacitance to two capacitors, e.g., $Cx1$ and $Cx2$, in a sensor circuit can be used for adjusting capacitive imbalance between $Cx1$ and $Cx2$ using the methods and systems of the present invention. The capacitive value of the top plate, such a the porous top plate of a humidity sensor, can be determined by monitoring a closed loop circuit of $Cx1$ and $Cx2$ to detect capacitive values of $Cx1$ and $Cx2$. Imbalances between $Cx1$ and $Cx2$ can be corrected by creating voids in the top plate, to thereby keep the values of $Cx1$ and $Cx2$ substantially equal.

It is therefore an object of the invention to provide and methods and systems for balancing the capacitance of a common top plate in a sensor, such as a relative humidity sensor.

In accordance with yet another aspect of the present invention, the capacitance balancing method can employ an area reduction technique for balancing capacitance in a common top plate of a sensor's structure, by minimizing the plate area to correct any error due to unbalanced capacitance introduced by the top plate.

In accordance with yet another aspect of the present invention, the area of a top plate can be minimize by using a system for creating voids, which can include a precision cutting instrument, a measuring device for enabling the measurement of capacitance of at least one of the common series capacitive circuit, $Cx1$ and $Cx2$, and power provided from a voltage source.

Additional objects and advantages of the invention will become apparent to those skilled in the art upon reference to the detailed description taken in conjunction with the provided figures.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and together with the detailed description of the invention, serve to explain the principles of the present invention.

FIG. 4 is a cut-away side view of a humidity sensor in accordance with a preferred embodiment of the present invention wherein;

DETAILED DESCRIPTION OF THE INVENTION

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the scope of the invention will become apparent to those of skill in the art from the detailed description of the invention and claims that follow.

Figure 1:
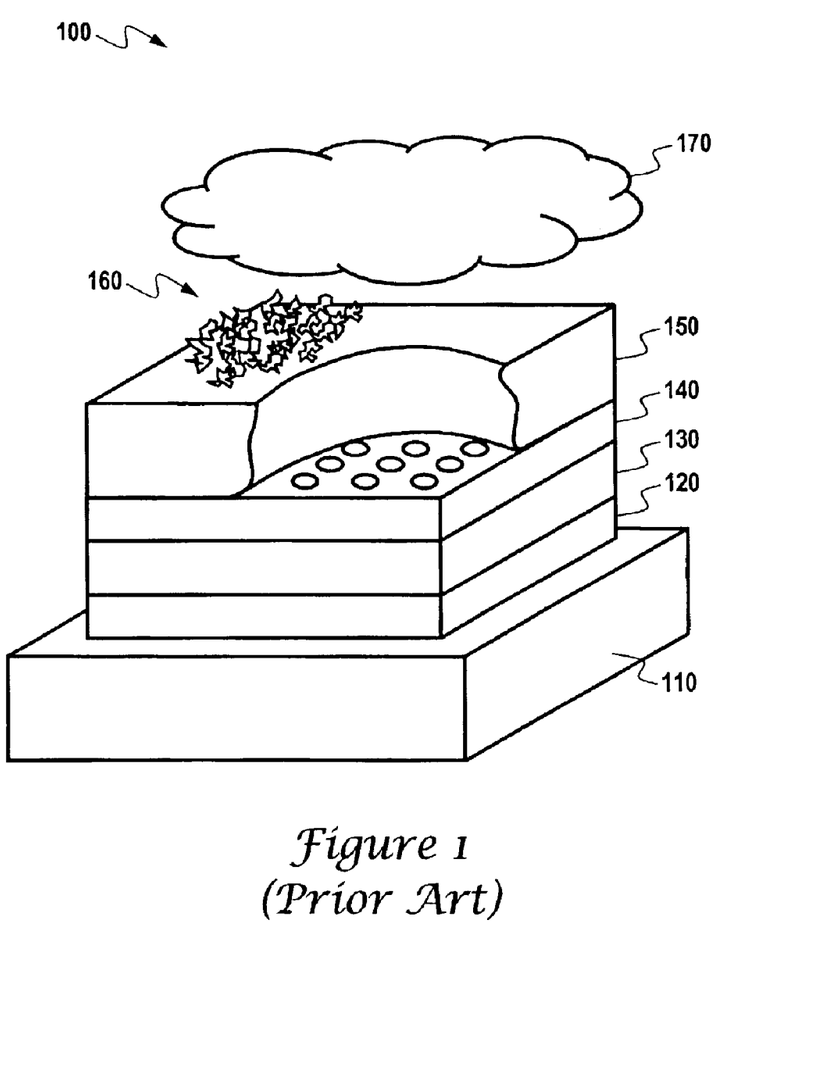
FIG. 1 is an illustration of a prior art humidity sensor.

Referring to FIG. 1 (labeled prior art), a perspective view of the basic components found in a semiconductor-based humidity sensor 100 is shown. A semiconductor humidity sensor 100 is generally grown on a silicon substrate 110. The active sensor components include a lower 120 and an upper 140 electrically conductive plates sandwiching a humidity sensing medium 130, such as a polymer. The polymer material is sensitive to humidity, and its electrically conductive properties (resistance and/or capacitance) change as it absorbs moisture or as it dries. Lower 120 and upper 140 plates are electrically connected to sensor circuitry (not shown). A protective layer 150 can be used to protect the active components of the sensor (e.g., top plate 120 and sensing medium 130) from debris 160. Upper plate 140 is designed to be porous in order to enable humidity to enter into the sensing medium from an external environment of interest 170 (the monitored environment of interest).

Figure 2:
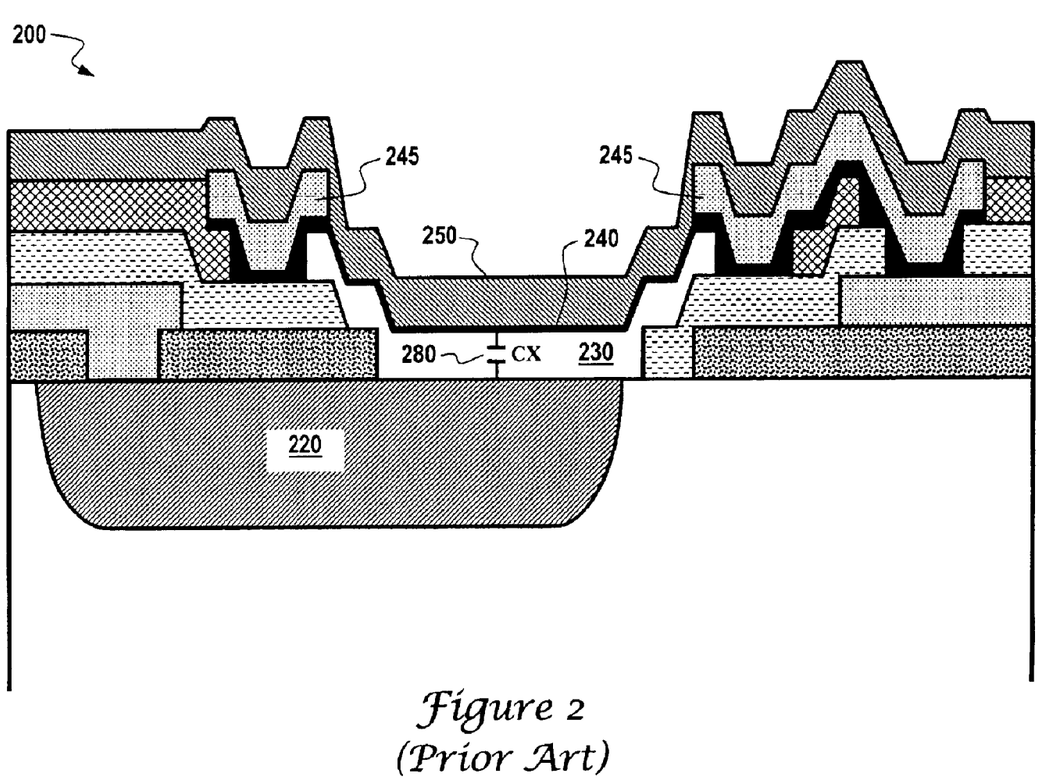
FIG. 2 is a cut-away side view of a prior art humidity sensor.

Referring to FIG. 2 (labeled prior art), an Integrated Relative Humidity Sensor (IRHS) that has been manufactured and sold by Honeywell, the present assignee, is illustrated. The illustrated semiconductor sensing system uses a planar humidity sensitive capacitor structure 200 that includes a thin porous platinum metal top plate 240 (top porous plate) covered by a protective polymer layer 250, and a humidity sensitive polyamide dielectric 230 sandwiched between the top porous plate 240 and a silicon bottom plate 220 (or substrate). The top plate 240, the polyamide dielectric 230 and the bottom plate 220 are at the heart of the capacitor function. Capacitance (Cx) formed with these three components is symbolized schematically in the drawing as 280. Variations in humidity affecting the dielectric 230 create a variable capacitive value between the top porous plate 240 and bottom plate 220.

The top porous plate 240 makes an electrical connection to chip electronics by contacting the thick aluminum interconnects 245. It has been found that the large step height between what consists of a very thin and porous conductive layer as the top porous plate 240 and the thick aluminum interconnects 245 tend to result in the formation of a weak mechanical connection. A common sensor failure mechanism is found when this weak mechanical connection breaks down during thermal/humidity cycling of the sensing device 200 due to the relatively high Temperature Coefficient of Expansion (TCE) of the sensing medium 230 (polyamide dielectric) and its swelling and shrinking due to changing humidity, which can physically keep the sensing capacitor from effective operation.

Figure 3:
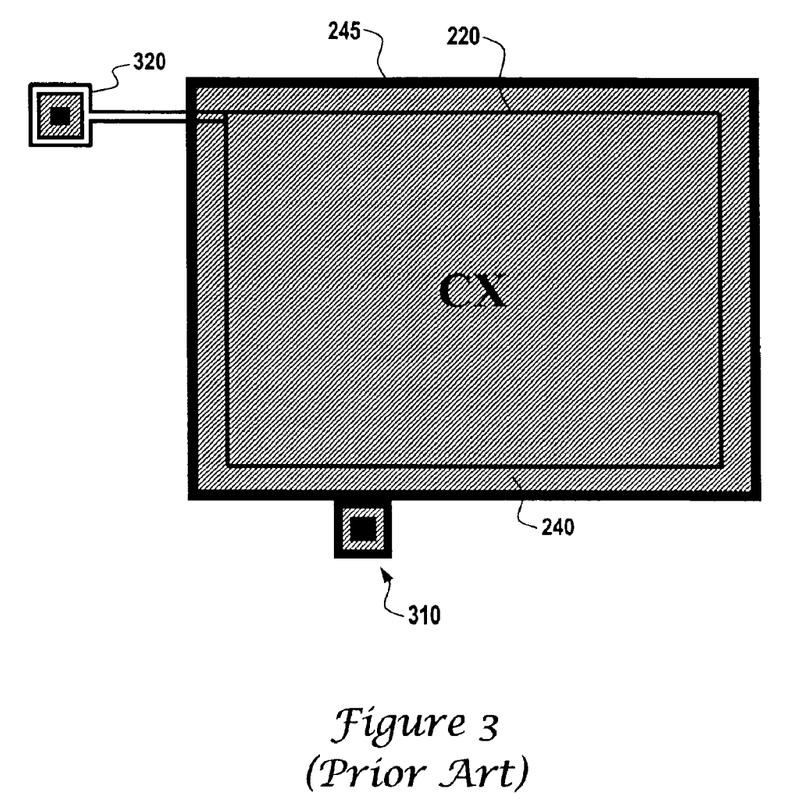
FIG. 3 is a top plan view of the prior art humidity sensor of FIG. 2.

FIG. 3 (labeled prior art) illustrates a top plan view of the top porous plate 240 layer of the prior art humidity sensor shown in FIG. 2. As seen in FIG. 3, top porous plate 240 is electrically connected with an electrical contact 310. Bottom plate 220 (P silicon) is also electrically connected to an electrical contact 320. The border area represents the interconnects 245 to which the top porous layer 240 becomes electrically connected during fabrication. It is along the interconnects 245 where the top porous plate 240 can become electrically detached due to expansion of the sensing medium (not shown). The top porous plate 240 is shown as one large conductive layer operating as a first plate of the humidity sensing capacitor, whereas the bottom plate operates as the second plate of the humidity sensing capacitor.

Figure 4:
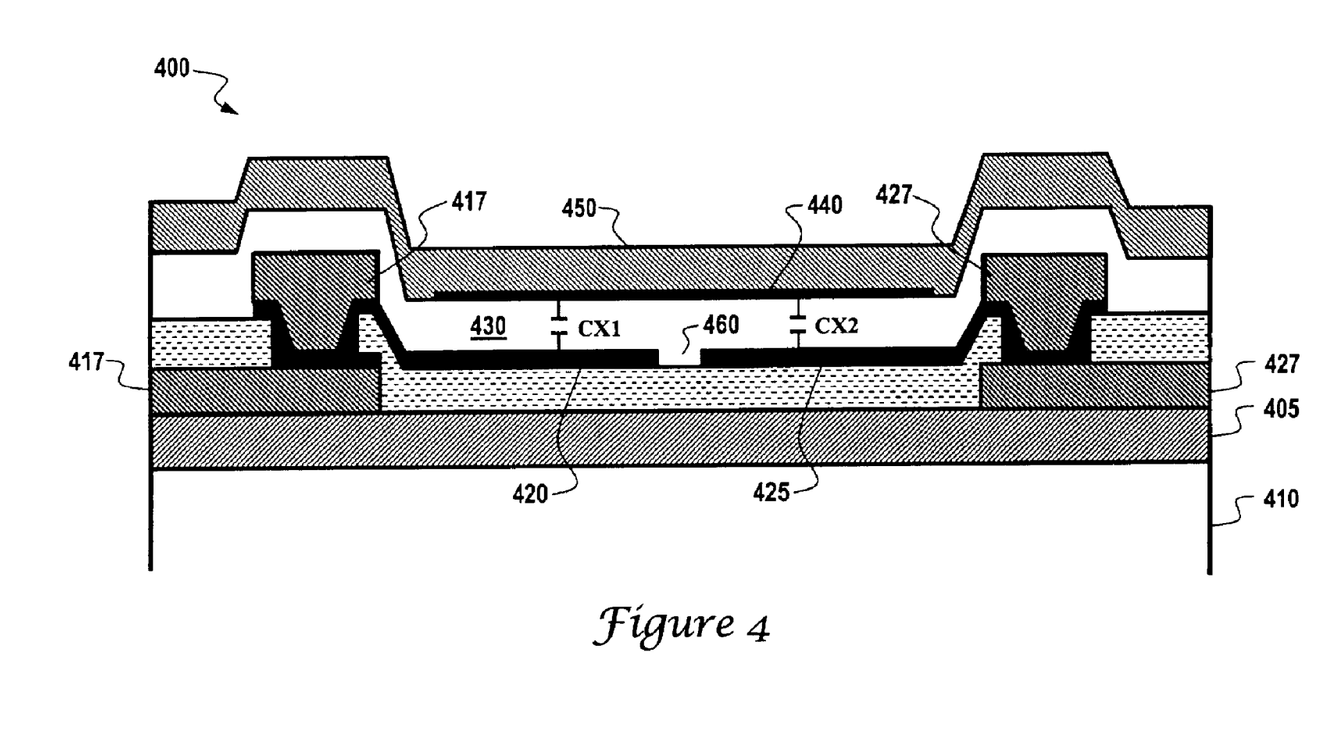

Referring to FIG. 4, a new capacitor configuration in accordance with the present invention will now be described for an improved semiconductor-based humidity sensor 400. The humidity sensor of the present invention includes a substrate 410. Insulating materials 405 can function as a buffer between the substrate 410 and first 420 and second 425 lower contact plates. First lower contact plate 420 is electrically connected to a first connector 417. Second lower contact plate 425 is electrically connected to a second connector 427. A sensing medium 430 is disposed on top of the first 420 and second 425 lower contact plates. A porous platinum top plate 440 is then disposed on top of the sensing medium 430. A breathable or porous protective layer 450 can also be disposed on top of the top plate for protection of the top plate 440 and sensing medium layer 430. Two capacitors Cx1 and Cx2 are schematically illustrated in respective positions within the sensing medium 430 between the first lower contact plate 420 and top plate 440 and the second lower contact plate 425 and the top plate 440. The gap/barrier 460 formed as an electrical disconnect between first 420 and second 425 lower contact plates creates the series capacitor configuration for Cx1 and Cx2.

Figure 5:
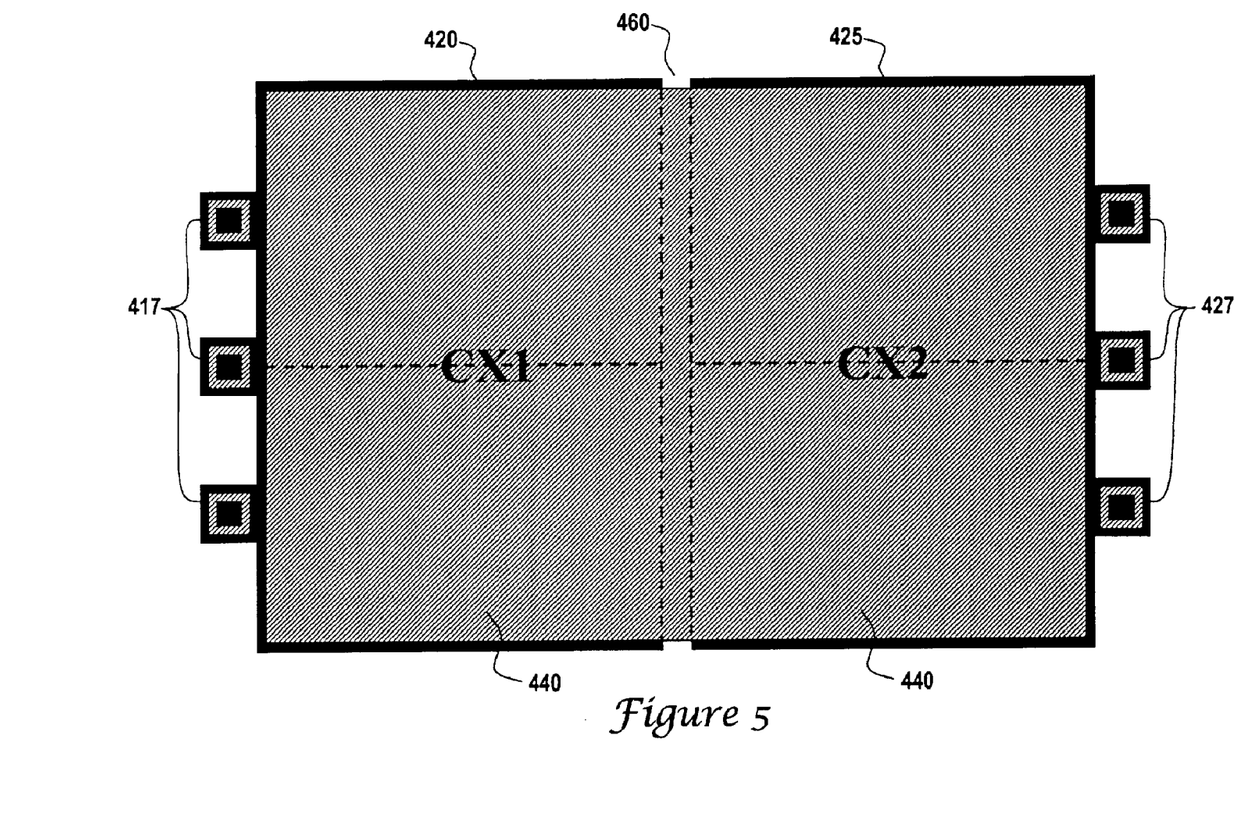
FIG. 5 is a top plan view of the humidity sensor of FIG. 4.

Referring to FIG. 5, a representative top view of the capacitive plates that provide electrical contact for generating capacitance through a sensing medium (not shown) for the present invention is shown. As shown in FIG. 5, capacitor Cx1 includes common top plate 440 (common to both Cx1 and Cx2) and a first lower contact plate 420 in further electrical contact with a first electrical contact 417. Capacitor Cx2 includes common top plate 440 as its first contact and second lower contact plate 425, which is in further electrical contact with second electrical contact 427. As shown in FIG. 5, a conductive barrier or insulating gap 460 is provided between the lower contact plates 420 and 425. This gap controls stray capacitance in parallel with Cx1 and Cx2, and controls parasitic capacitance between common top plate 440 and the underlying silicon substrate 410 (shown in FIG. 4). In the preferred embodiment, the gap 460, which can also be seen in FIG. 4 between the lower contact plates, near the center of the device, is filled with the humidity-sensitive dielectric (although other dielectrics could be utilized).

The capacitive values of Cx1 and Cx2 must not only be physically realized using the gap/barrier shown in FIGS. 4 and 5, but also adjusted for the device to operate properly (i.e., calibrated). It is known in the art to control or adjust capacitance through variable capacitors. In the present invention, however, it is not feasible to provide for ongoing capacitive control. Therefore, the present inventors have devised methods of adjusting the capacitive values of Cx1 and Cx2 while keeping their values substantially equal prior to applying a protective layer 450 as shown in FIG. 4 and/or packaging the device. The present inventors have also determined systems that can be used to carry out their methods.

Figure 6:
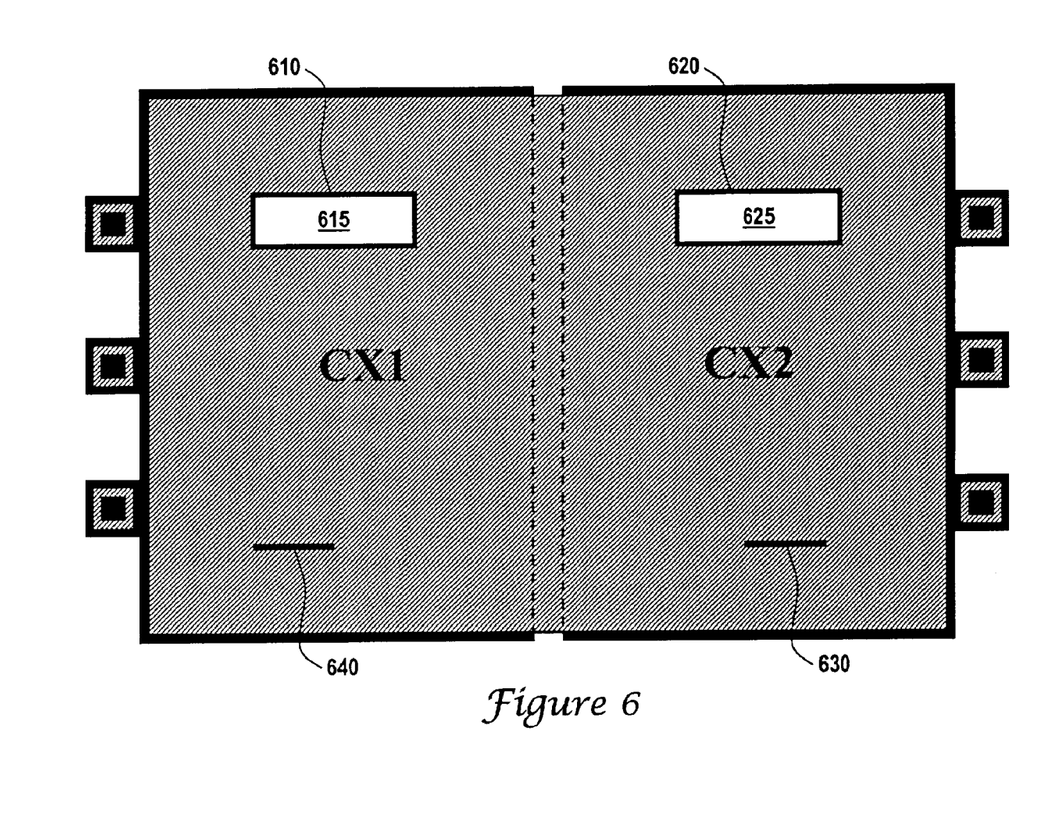
FIG. 6 is an illustration of another embodiment of the present invention wherein conductivity of the top plate is modified through area reduction in order to balance capacitance between $Cx1$ and $Cx2$.

Referring to FIG. 6, a representative top view of the capacitive plates that provide electrical contact for generating capacitance through a sensing medium (not shown) for the present invention is illustrated. As shown in FIG. 6, the common top plate 440 (common to both Cx1 and Cx2) has been removed or etched at three locations. A first location relative to Cx1 shows a box-like etching 610 on common top plate 440, and a second location relative to Cx2 shows box-like etching 620. An etching procedure will cut through the entire common top plate 440 layer, effectively removing capacitive value associated with box-like areas 615 and 625 of the common top plate 440. The resulting area available for electron build-up on the plate 440 is thereby lessened, thus lowering the capacitive value of Cx1 and Cx2. Care is taken to make areas 615 and 625 approximately equal. It should be appreciated by those skilled in the art, however, that circumstances may warrant that areas on the top plate 440, such as those depicted by areas 615 and 625, should not be equal in order to achieve capacitive balancing or even diverse values between Cx1 and Cx2. It should also be appreciated by those skilled in the art that areas or voids can be introduced into a top plate of a sensor, such as top plate 440, using systems currently known in the art for removing material within the semiconductor art. For example, systems such as etching equipment, lasers and precise mechanical cutting instruments and other precision cutting instruments known in the art can be used within a system to carry out the methods of the present invention. A system would require measuring devices known in the art for enabling the measurement of capacitance, such as oscilloscopes, microprocessor-based analytical tools and other measuring devices. A voltage source would be required to provide power to the series capacitive circuit during measurement. Voltage can also be applied during cutting of the top plate. Voltage sources (DC and AC) are also well known in the art. It is preferable that the voltage source provides a constant voltage during measuring and/or cutting.

As seen on the top common plate 440 area associated with Cx2, a slit 630 and/or 640 has also been etched into the top common plate 440. The purpose of etching slits 630 and/or 640 is similar in reason to that of creating the box-like areas 625 and 615, which was to reduce the amount of common top plate 440 area that will contribute to the overall capacitance of either or both Cx1 or Cx2.

The initial adjustments made to Cx1 (615) and Cx2 (625) can be seen as coarse adjustments to the net value of the sensing capacitance, whereas slits 640 and 630 can be seen as fine adjustments. The etching procedure can be used anywhere on the top plate deemed necessary in order to adjust the net capacitance of Cx1 and Cx2, while keeping the values of Cx1 and Cx2 substantially equal. It should be appreciated to those skilled in the art from the foregoing discussion that adjustments can be carried out in a series of etchings and with etchings of various shapes and sizes. Any adjustments will generally be carried out while trying to maintain equality in value between Cx1 and Cx2.

Figure 7:
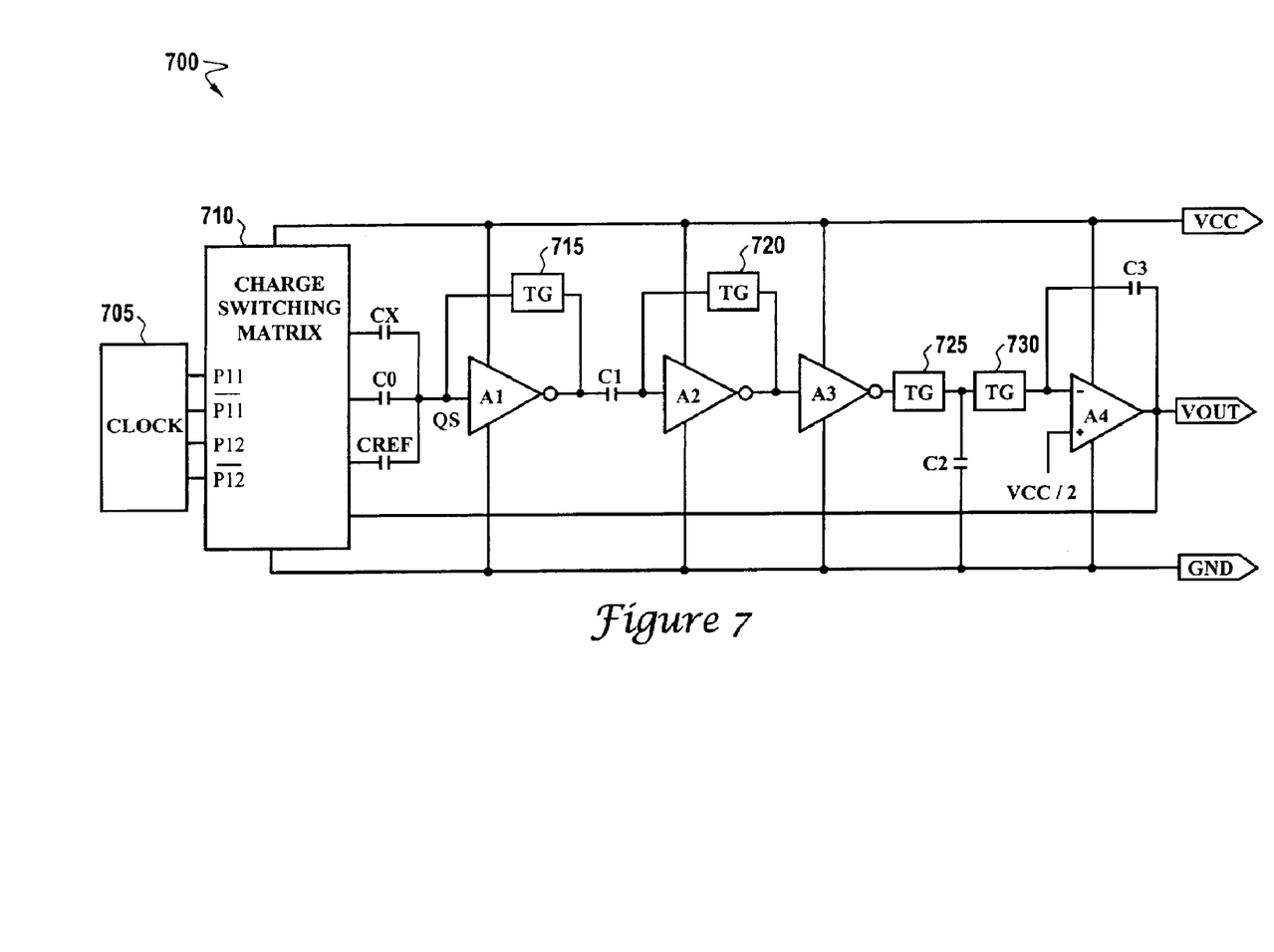
FIG. 7 illustrates relative humidity-to-voltage transfer function components.

The charge balancing method used to transduce relative humidity to a linear voltage will now be described. Most linear control circuits are utilized to regulate voltages or currents; however, the high impedance capacitive nature of the humidity sensor is more readily handled by control of charge. FIG. 7 shows the essential components that comprise the relative humidity-to-voltage transfer function in terms of a circuit diagram 700. C0, C1, C2, C3, and Cref are all capacitors that are designed to be insensitive to humidity and that are fabricated at the same time and from the same materials. Thus, while their absolute values of capacitance will vary, the ratios will track very closely. Cx is designed to be sensitive to humidity and is fabricated at a different time and from different materials than the aforementioned capacitors. The switching matrix 710 varies the wiring scheme for capacitors: Cx, C0, and Cref using two-phase, non-overlapping, dual polarity clocks, as can be provided by clock generator 705. Note that one end of all three capacitors is always connected in common, thus providing a charge summing node, Qs. Inverters A1, A2, and A3, and capacitor C1, and the pair of associated transmission gates 715 and 720 form a high gain comparator. C2 and its pair of associated transmission gates 725 and 730 are the switched capacitor equivalent of a resistor which coupled with amplifier A4 and feedback capacitor C3 form an integrator.

Figure 8:
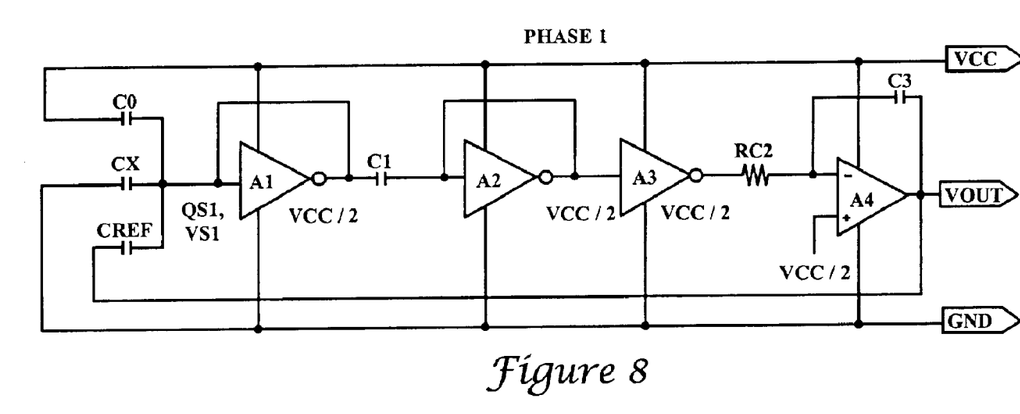
FIG. 8 illustrates circuit connectivity for operation during a Phase 1 operation.
Figure 9:
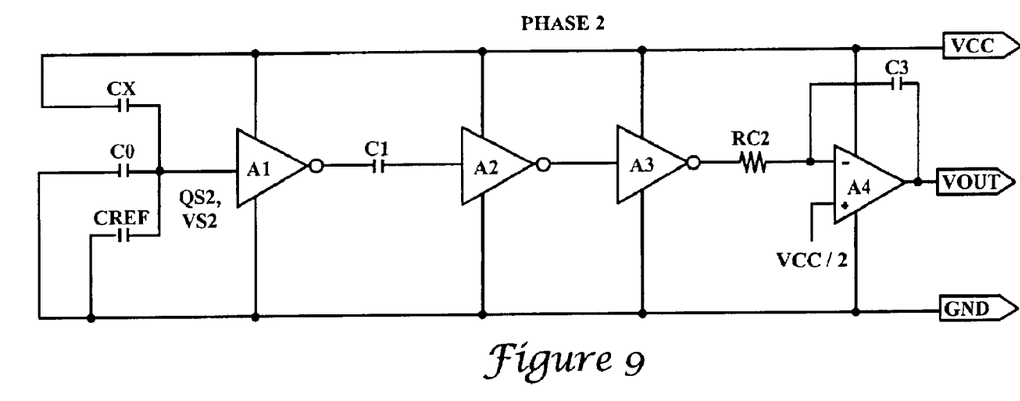
FIG. 9 illustrates circuit connectivity for operation during a Phase 2 operation.

FIGS. 8 and 9 show the circuit connectivity for operation during "Phase 1" and "Phase 2" respectively. Neglecting Cref for the moment and concentrating on C0 and Cx, note that they effectively form a voltage divider. In Phase 1 C0 is pulled up to Vcc and Cx is pulled down to GND and vice versa during Phase 2. Thus a periodic differential voltage is created which is a function of the difference in capacitance values. Those skilled in the art will recognize this as a half bridge sensor configuration. During Phase 1, inverters A1 and A2 short their input node to their output node, which, when implemented with complementary FETs, forms a voltage divider.

FIG. 8 indicates that all three of these FETs are designed to produce a half supply transfer function in this configuration, thus driving both the charge summing node and the output of A3 to Vcc/2 during Phase 1. These transmission gate shorts are opened up during Phase 2, creating a high gain inverting comparator, which allows small movement in the charge summing node voltage relative to Vcc/2 to drive the output of A3 to Vcc or GND. Thus A3, the output of the comparator, controls the integrator. During Phase 1, the output of A3 and the non-inverting input of A4 are both at Vcc/2, which puts the integrator into a "Hold" state. So Phase 1 can be thought of as a measurement or sampling phase during which Cref is charged. During Phase 2, Cref is disconnected from the integrator output and reconnected to GND and the comparator responds to the charge-summing node. If the comparator output goes to GND, then the output of the integrator increases linearly. If the comparator output goes to Vcc, then the output of the integrator decreases linearly. If the charge-summing node effectively remains at Vcc/2 during Phase 2, then the integrator remains in the "Hold" state, though this is rarely the case. So Phase 2 can be thought of as the negative feedback adjustment phase.

The following equations mathematically describe the operation of the aforementioned circuit. Equations 1 and 2 calculate the charge at the summing node during Phase 1 and 2, respectively. The negative feedback results in Qs1 and Vs1 being substantially equal to Qs2 and Vs2. Equation 3 mathematically describes the resulting transfer function for the complete circuit operation.

$$Qs1 = Cx \cdot Vs1 + C0 \cdot (Vs1 - Vcc) + Cref \cdot (Vs1 - Vout) \quad \text{EQ. 1}$$

$$Qs2 = Cx \cdot (Vs2 - Vcc) + C0 \cdot Vs2 + Cref \cdot Vs2 \quad \text{EQ. 2}$$

$$Vout = \left(\frac{Cx}{Cref}\right) \cdot Vcc - \left(\frac{C0}{Cref}\right) \cdot Vcc \quad \text{EQ. 3}$$

Figure 10:
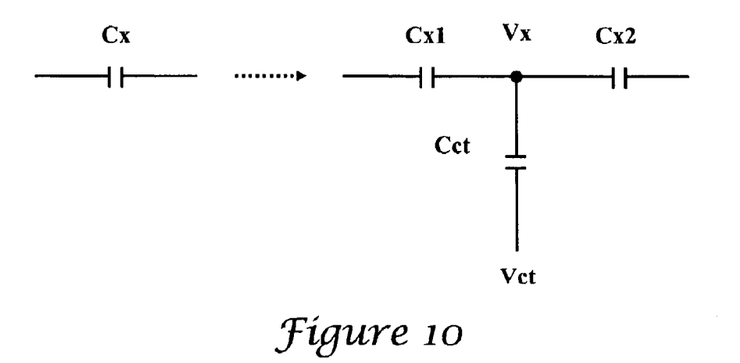
FIG. 10 illustrates a parasitic capacitance included in an analysis of humidity sensor circuitry to understand the parasitic capacitances influence on a transfer function during circuit operation.

As described previously, the new construction method for the humidity sensitive capacitor, Cx, minimizes the problems due to mechanical weakness found in previous construction methods. As shown in FIG. 10, however, this present invention creates a parasitic capacitance, Cct, which is included in the analysis to understand its influence on the transfer function for the complete circuit operation. Equation 4 mathematically describes the new transfer function, including the effect of the parasitic capacitor, Cct, and mismatch (mm) between Cx1 and Cx2.

$$Vout = \left( \frac{4 \cdot Cx^2 \cdot (1 - mm^2)}{(4 \cdot Cx + Cct) \cdot Cref} \right) \cdot Vcc - \left( \frac{C0}{Cref} \right) \cdot Vcc \qquad \text{EQ. 4}$$

Note that if the parasitic capacitance, Cct, is much less than four (4) times Cx, and the squared mismatch, $mm^2$, between Cx1 and Cx2 is much less than one, then Equation 4 simplifies back to Equation 3. Therefore, the parasitic capacitance from the floating interconnection to the underlying silicon should be minimized. Also, since the interconnection, Vx, is electrically floating, charge build-up on the top surface of the chip is minimized to avoid destructive breakdown of the sensing capacitors. And, as shown in FIG. 6 and discussed previously, the adjustments made to Cx should be divided substantially equally between Cx1 and Cx2 to minimize the sensitivity reduction due to mismatch error.

The present device is used to sense the relative humidity in the ambient environment around the sensor. During operation, a relative humidity level is sensed and then the sensor generates a voltage output proportional to the relative humidity. This voltage can then be used by other circuits to implement functions such as relative humidity control, enthalpy control for building HVAC, weather sensing instruments, process controls for drying, process controls for batch or continuous production where relative humidity is a parameter that controls the output of a process or is related to some process variable to be controlled, length or end of cycle in drying applications, and other applications.

The embodiment and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive nor to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A method for balancing capacitance of a top plate associated with at least two capacitors to provide a common series capacitive circuit in a semiconductor-based humidity sensor, comprising the steps of:
   (a) providing a humidity sensor having a series capacitive circuit including a common top plate for first and second capacitors, Cx1 and Cx2 respectively, Cx1 further comprising a first bottom plate and Cx2 further comprising a second bottom plate, said common top plate, Cx1 and Cx2 being separated by a common, humidity-sensitive dielectric material wherein changes in humidity affect said common, humidity sensitive dielectric material and thereby changes the capacitive value of said series capacitive circuit;
   (b) conducting capacitive measurement of said first and second capacitors by sampling signals rendered by said first and second capacitors while connected in series in a closed loop circuit to determine the capacitive values of Cx1 and Cx2 during said measuring cycle; and
   (c) adjusting the capacitive values of Cx1 and Cx2 by creating voids in said top plate to keep the values of Cx1 and Cx2 substantially equal.

2. The method of claim 1, wherein step (b) further comprises the steps of:
   charging said series capacitive circuit to a fixed voltage;
   monitoring said closed loop circuit to detect capacitive value of Cx1 and Cx2 provided by the top plate and dielectric associated with Cx1 and Cx2.

3. The method of claim 1, further comprising the steps of:
   (d) charging said series capacitive circuit to a fixed voltage;
   (e) monitoring said closed loop circuit to detect any change in capacitive value of Cx1 and Cx2 provided by said adjusting step.

4. The method of claim 3, repeating steps (d) and (e) until a desired capacitive value for at least one of Cx1 and Cx2 is achieved.

5. The method of claim 4, said repeating of steps (d) and (e) until a desired capacitive value for at least one of Cx1 and Cx2 is achieved is carried out while maintaining said fixed voltage charge over the series capacitive circuit.

6. The method of claim 3, repeating steps (d) and (e) while maintaining said fixed voltage charge over the series capacitive circuit until a desired capacitive value for at least one of Cx1 and Cx2 is achieved.

7. The method of claim 6, said repeating of steps (d) and (e) until a desired capacitive value for at least one of Cx1 and Cx2 is achieved is carried out while maintaining said fixed voltage charge over the series capacitive circuit and considering any affect of changes in said common humidity sensitive dielectric material over said capacitive value.

8. The method of claim 6, repeating steps (d) and (e) while maintaining said fixed voltage charge over the series capacitive circuit until a desired capacitive value for at least one of Cx1 and Cx2 is achieved is carried out while maintaining said fixed voltage charge over the series capacitive circuit and considering any affect of changes in said common, humidity sensitive dielectric material over said capacitive value.

9. The method of claim 6, repeating steps (d) and (e) until a desired capacitive value for at least one of Cx1 and Cx2 is achieved while said common humidity sensitive dielectric material is kept dry.

10. A method for balancing capacitance of a top plate associated with at least two capacitors to provide a common series capacitive circuit in a semiconductor-based relative humidity sensor, comprising the steps of:
   (a) providing a humidity sensor having a series capacitive circuit including a common top plate for first and second capacitors, Cx1 and Cx2 respectively, Cx1 further comprising a first bottom plate and Cx2 further comprising an associated with second bottom plate, said common top plate, Cx1 and Cx2 being separated by a common humidity sensitive dielectric material;
   (b) charging said series capacitive circuit to a fixed voltage;
   (c) sampling capacitive value of Cx1 and Cx2 provided by the top plate and dielectric associated with Cx1 and Cx2 while connected in series in a closed loop circuit to determine the capacitive values of Cx1 and Cx2;

(d) adjusting the capacitive values of Cx1 and Cx2 by creating voids in said top plate to keep the values of Cx1 and Cx2 substantially equal; and (e) monitoring said closed loop circuit to detect changes in capacitive value of Cx1 and Cx2 provided by step (d).

11. The method of claim 10, repeating steps (d) and (e) until a desired capacitive value for at least one of Cx1 and Cx2 is achieved.

12. The method of claim 10, repeating steps (d) and (a) until a desired capacitive value for at least one of Cx1 and Cx2 is achieved is carried out while maintaining said fixed voltage charge over the series capacitive circuit.

13. The method of claim 10, repeating steps (d) and (e) while maintaining said fixed voltage charge over the series capacitive circuit until a desired capacitive value for at least one of Cx1 and Cx2 is achieved.

14. The method of claim 10 wherein changes in humidity affect said humidity sensitive dielectric and thereby change the capacitive value of said series capacitive circuit.

15. The method of claim 14, repeating steps (d) and (e) until a desired capacitive value for at least one of Cx1 and Cx2 is achieved.

16. The method of claim 10, said repeating of steps (d) and (e) until a desired capacitive value for at least one of Cx1 and Cx2 is achieved is carried out while maintaining said fixed voltage charge over the series capacitive circuit and while considering how any changes in said humidity sensitive dielectric can affect said capacitive value.

17. The method of claim 14, repeating steps (d) and (e) while maintaining said fixed voltage charge over the series capacitive circuit until a desired capacitive value for at least one of Cx1 and Cx2 is achieved is carried out while considering how humidity affecting changes in said humidity sensitive dielectric can affect said capacitive value.

18. The method of claim 10, repeating steps (d) and (e) until a desired capacitive value for at least one of Cx1 and Cx2 is achieved while said humidity sensitive dielectric is kept dry.

19. A system for balancing the capacitance of a common top plate associated with at least two capacitors, Cx1 and Cx2, of a common series capacitive circuit in a semiconductor-based humidity sensor, wherein said common top plate, a first plate associated with Cx1, a second plate associated and Cx2, and a common humidity sensitive dielectric material separating said top plate, said first plate and said second plate comprise said common series capacitive circuit, said system comprising:

a precise cutting instrument for creating voids within said common top plate, wherein;

a measuring device for determining the capacitive value of at least one of said; said common capacitive circuit, Cx1 and Cx2; and a voltage source for providing a constant voltage to said series capacitive circuit;

wherein changes in humidity affect said common, humidity sensitive dielectric material and thereby changes the capacitive value of said series capacitive circuit.

* * * * *